United States Patent
Wang et al.

(10) Patent No.: US 8,639,352 B2
(45) Date of Patent: Jan. 28, 2014

(54) WIRE CONFIGURATION AND METHOD OF MAKING FOR AN IMPLANTABLE MEDICAL APPARATUS

(75) Inventors: Ling Wang, Plymouth, MN (US); Bernard Q. Li, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 279 days.

(21) Appl. No.: 12/419,082

(22) Filed: Apr. 6, 2009

(65) Prior Publication Data

US 2010/0256718 A1 Oct. 7, 2010

(51) Int. Cl.
*A61N 1/04* (2006.01)

(52) U.S. Cl.
USPC ..... 607/116; 607/115; 174/102 R; 174/126.1; 600/372

(58) Field of Classification Search
USPC .......... 607/115–117, 119, 122; 600/372, 373, 600/377, 374, 395, 396; 174/102 R, 103, 174/106 R, 108, 102 A, 126.1, 126.2
See application file for complete search history.

(56) References Cited

U.S. PATENT DOCUMENTS

| | | | | |
|---|---|---|---|---|
| 248,208 | A * | 10/1881 | Patterson | 174/89 |
| 284,423 | A * | 9/1883 | Hollingshead | 174/106 R |
| 630,634 | A * | 8/1899 | Sundh | 138/131 |
| 1,214,830 | A * | 2/1917 | Runzel | 174/107 |
| 1,626,776 | A * | 5/1927 | Austin | 174/128.1 |
| 1,756,319 | A * | 4/1930 | Wentz | 178/45 |
| 2,022,839 | A * | 12/1935 | Austin | 174/127 |
| 2,133,863 | A * | 10/1938 | Knoderer | 174/106 R |
| 2,211,790 | A * | 8/1940 | Pile | 74/502.6 |
| 2,677,765 | A * | 5/1954 | Collins et al. | 52/836 |
| 3,333,045 | A * | 7/1967 | Fisher et al. | 174/20 |
| 3,345,456 | A * | 10/1967 | Gilmore | 174/128.1 |
| 3,572,344 | A * | 3/1971 | Bolduc | 607/129 |

(Continued)

FOREIGN PATENT DOCUMENTS

| | | |
|---|---|---|
| EP | 1083243 | 3/2001 |
| EP | 1547647 A1 | 6/2005 |

(Continued)

OTHER PUBLICATIONS

PCT International Search Report and Written Opinion dated May 25, 2010.

(Continued)

*Primary Examiner* — Carl H Layno
*Assistant Examiner* — Eugene Wu
(74) *Attorney, Agent, or Firm* — Beth L. McMahon; Medtronic, Inc.

(57) ABSTRACT

A filar includes an inner conductive core that is formed of a low-resistivity material such as silver having a resistivity of less than 20 μΩ per centimeter. A conductive coil is provided around the core to form a filar. This coil is formed of a biocompatible alloy or super alloy having an ultimate tensile strength (UTS) of between 150 kilo pounds per square inch (ksi) and 280 ksi at room temperature. Examples of such alloys include CoCrMo, CoFeCrMo, and CoFeNiCrMo. In one specific embodiment, the alloy is MP35N (CoNiCrMo), which may be low-titanium ("low-ti") MP35N. One or more such filars may be included within a wire. This wire may be carried by an implantable medical apparatus such as a lead, lead extension, or catheter. The wire may electrically couple elements such as connector electrodes to conducting electrodes or sensors.

33 Claims, 8 Drawing Sheets

(56) References Cited

U.S. PATENT DOCUMENTS

| | | | |
|---|---|---|---|
| 4,411,168 A * | 10/1983 | Yoshifuji | 74/502.5 |
| 4,541,303 A * | 9/1985 | Kuzunishi | 74/502.5 |
| 4,559,951 A * | 12/1985 | Dahl et al. | 600/374 |
| 4,634,042 A * | 1/1987 | Smith | 228/173.4 |
| 4,678,868 A | 7/1987 | Kraska et al. | |
| 4,689,444 A * | 8/1987 | Burgess | 174/128.1 |
| 4,835,340 A * | 5/1989 | Muz | 174/119 R |
| 4,945,342 A | 7/1990 | Steinemann | |
| 5,103,543 A * | 4/1992 | Hodgson | 29/896.9 |
| 5,169,597 A | 12/1992 | Davidson et al. | |
| 5,303,704 A | 4/1994 | Molacek et al. | |
| 5,330,521 A | 7/1994 | Cohen | |
| 5,358,517 A | 10/1994 | Pohndorf et al. | |
| 5,366,493 A | 11/1994 | Scheiner et al. | |
| 5,385,578 A | 1/1995 | Bush et al. | |
| 5,423,881 A | 6/1995 | Breyen et al. | |
| 5,454,795 A * | 10/1995 | Samson | 604/526 |
| 5,477,864 A | 12/1995 | Davidson | |
| 5,483,022 A * | 1/1996 | Mar | 174/128.1 |
| 5,522,875 A | 6/1996 | Gates et al. | |
| 5,545,203 A | 8/1996 | Doan | |
| 5,584,873 A | 12/1996 | Shoberg et al. | |
| 5,649,967 A * | 7/1997 | De Bellis et al. | 607/9 |
| 5,683,442 A | 11/1997 | Davidson | |
| 5,685,306 A | 11/1997 | Davidson | |
| 5,760,341 A | 6/1998 | Laske et al. | |
| 5,796,044 A | 8/1998 | Cobian et al. | |
| 5,871,595 A | 2/1999 | Ahmed et al. | |
| 5,954,759 A * | 9/1999 | Swoyer et al. | 607/122 |
| 6,078,010 A * | 6/2000 | Funahashi et al. | 174/126.1 |
| 6,169,252 B1 | 1/2001 | Avellanet | |
| 6,200,685 B1 | 3/2001 | Davidson | |
| 6,238,491 B1 | 5/2001 | Davidson et al. | |
| 6,248,955 B1 * | 6/2001 | Avellanet | 174/128.1 |
| 6,399,886 B1 * | 6/2002 | Avellanet | 174/128.1 |
| 6,402,859 B1 | 6/2002 | Ishii et al. | |
| 6,409,852 B1 | 6/2002 | Lin et al. | |
| 6,475,169 B2 * | 11/2002 | Ferrera | 600/585 |
| 6,720,497 B1 * | 4/2004 | Barsne | 174/102 R |
| 6,752,882 B2 | 6/2004 | Lin et al. | |
| 6,800,153 B2 | 10/2004 | Ishii et al. | |
| 6,950,709 B2 | 9/2005 | Baudino | |
| 7,015,392 B1 * | 3/2006 | Dickenson | 174/36 |
| 7,130,700 B2 | 10/2006 | Gardeski et al. | |
| 7,174,220 B1 | 2/2007 | Chitre et al. | |
| 7,261,782 B2 | 8/2007 | Hwang et al. | |
| 7,519,432 B2 | 4/2009 | Bolea et al. | |
| 7,571,010 B2 | 8/2009 | Zarembo et al. | |
| 7,674,973 B2 * | 3/2010 | Cardas | 174/36 |
| 7,722,805 B2 | 5/2010 | Hoa et al. | |
| 7,745,732 B2 * | 6/2010 | Michael et al. | 174/126.1 |
| 2002/0099430 A1 | 7/2002 | Verness et al. | |
| 2002/0174922 A1 | 11/2002 | Ishii et al. | |
| 2003/0009095 A1 | 1/2003 | Skarda | |
| 2004/0064174 A1 | 4/2004 | Belden | |
| 2004/0064175 A1 | 4/2004 | Lessar et al. | |
| 2004/0099436 A1 * | 5/2004 | Maekawa et al. | 174/128.1 |
| 2004/0158309 A1 | 8/2004 | Wachter et al. | |
| 2004/0267342 A1 | 12/2004 | Alinder et al. | |
| 2005/0070990 A1 | 3/2005 | Stinson | |
| 2005/0072496 A1 | 4/2005 | Hwang et al. | |
| 2005/0222659 A1 | 10/2005 | Olsen et al. | |
| 2006/0089691 A1 * | 4/2006 | Kaplan et al. | 607/116 |
| 2007/0137742 A1 | 6/2007 | Hao et al. | |
| 2007/0193662 A1 | 8/2007 | Jablokov et al. | |
| 2008/0195194 A1 | 8/2008 | Pacetti et al. | |
| 2008/0294207 A1 | 11/2008 | Kast et al. | |
| 2008/0312740 A1 | 12/2008 | Wachter et al. | |
| 2010/0075168 A1 | 3/2010 | Schaffer | |
| 2012/0211255 A1 * | 8/2012 | Senet | 174/108 |
| 2012/0271385 A1 * | 10/2012 | Li et al. | 607/116 |
| 2012/0271386 A1 * | 10/2012 | Li et al. | 607/116 |

FOREIGN PATENT DOCUMENTS

| | | |
|---|---|---|
| JP | 20010200939 | 1/2003 |
| WO | 9945161 | 9/1999 |
| WO | 01/91851 | 6/2001 |
| WO | 2009145406 | 12/2009 |

OTHER PUBLICATIONS

Iman, et al, "Titanium Alloys As Implant Materials", ASTM Special Technical Publication, Philadelphia, PA, US, No. 1272, Nov. 16, 1994, pp. 3-16.

Ribeiro, Al, Mechanical, physical, and chemical characterization of Ti-35Nb-5Zr and Ti-35Nb-10Zr casting alloys, J Mater Sci Mater Med. Aug. 2009;20(8):1629-36. Epub Apr. 1, 2009.

Ti-075 Ti-15Mo.pdf.

http://en.wikipedia.org/wiki/Titanium_alloy.

* cited by examiner

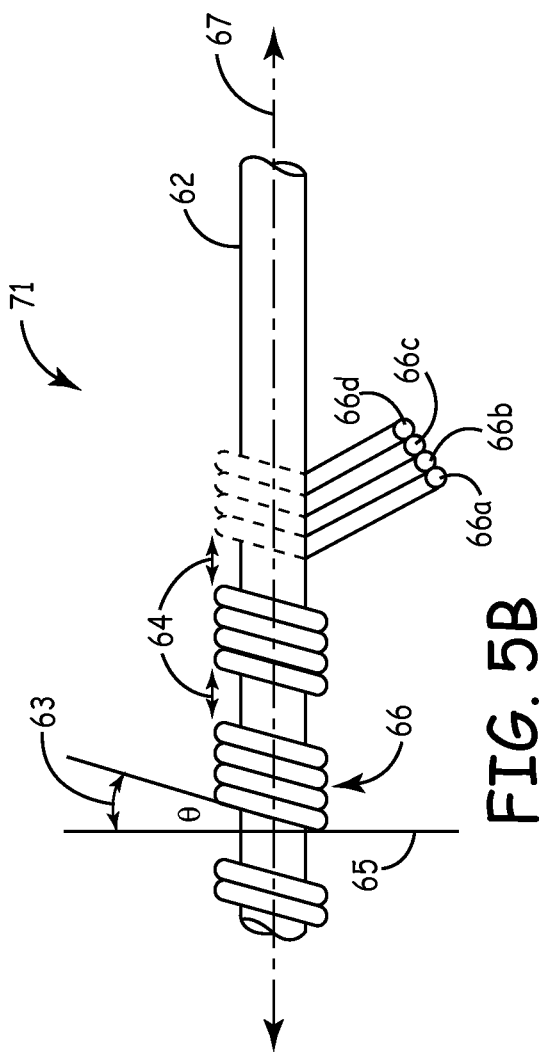
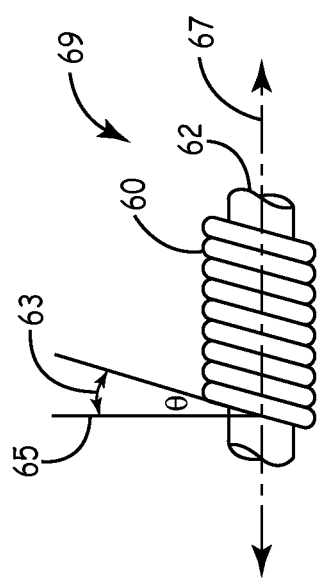
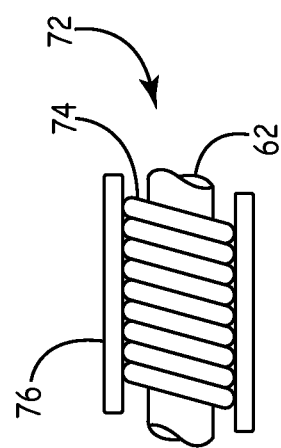
FIG. 5B
FIG. 5A
FIG. 5C

WIRE CONFIGURATION AND METHOD OF MAKING FOR AN IMPLANTABLE MEDICAL APPARATUS

FIELD OF THE INVENTION

This invention relates to a medical apparatus and more particularly to a wire configuration for a medical apparatus such as a lead or lead extension.

BACKGROUND

The medical device industry produces a wide variety of electronic and mechanical devices for treating patient medical conditions such as pacemakers, defibrillators, neurostimulators and therapeutic substance delivery pumps. Medical devices can be surgically implanted or connected externally to the patient receiving treatment. Clinicians use medical devices alone or in combination with therapeutic substance therapies and surgery to treat patient medical conditions. For some medical conditions, medical devices provide the best and sometimes the only therapy to restore an individual to a more healthful condition. One type of medical device is an implantable neurological stimulation system that can be used to treat conditions such as pain, movement disorders, pelvic floor disorders, gastroparesis, and a wide variety of other medical conditions. The neurostimulation system typically includes a neurostimulator that is typically connected to a stimulation lead that has one or more electrodes to deliver electrical stimulation to a specific location in the patient's body.

Current leads that incorporate straight bundled-stranded-wire ("bsw") wire have the weakness that all axial loading is transmitted, through the wires, to the electrical connections at either end of the device. This type of configuration can not provide kink resistance. One way to make this type of design more kink resistant is to provide a tubular encasing surrounding each wire. Such tubular encasing is optimally made of a material possessing a high tensile strength. Providing this tubular strengthening member may complicate the manufacturing process, however. What is needed is a more kink-resistant design that is both efficiently manufactured and that provides superior conductivity.

SUMMARY OF THE INVENTION

According to one embodiment, an improved conductive wire is disclosed for use in connecting conductive elements of the type included in a medical electrical lead. The wire may include one or more filars. Each such filar includes an inner conductive core that is formed of a low-resistivity (highly conductive) material and coil formed around this core. The coil is made of a biocompatible alloy having an ultimate tensile strength (UTS) of between 150 kilo pounds per square inch (ksi) and 280 ksi at room temperature.

In one embodiment, the material used to form the inner conductive core possesses a resistivity of less than 20 µΩ per centimeter. For instance, this core may be formed of silver. In other embodiments, this core may be formed of tantalum, tantalum alloys, niobium, niobium alloys, platinum and platinum alloys, and palladium and palladium alloys. Other materials possessing a resistivity of less than 20 µΩ per centimeter may be used instead.

As previously mentioned, the coil formed around the inner core is made of a biocompatible alloy having a UTS of between 150 ksi and 280 ksi at room temperature. Examples of such super alloys include CoCrMo, CoFeCrMo, and CoFeNiCrMo. In one specific embodiment, the super alloy is MP35N (CoNiCrMo), which may be low-titanium ("low-ti") MP35N or a higher titanium variety of MP35N. Other biocompatible cobalt-based, nickel-based or titanium-based alloys and super alloys may be used in the alternative. For instance, Ti-15Mo is one example of a titanium-based alloy suitable for this purpose.

The coil that is formed around the core may comprise one or more conductive filaments. The filaments may be wound around the core at a selected angle of between 0 and 45 degrees. Generally, these filaments are wound around the core together.

Each of the conductive filaments included in the coil is formed by annealing the selected conductive alloy above the melting point of the conductive core. The alloy is then drawn to a desired diameter, which in one embodiment is between 0.03 millimeters and 0.10 millimeters, to form a filament. The filament may then be wound around the conductive core to form a filar.

As previously mentioned, one or more filars manufactured according to techniques described herein may be bundled in a wire, either by twisting the filars together to form a cable, or by allowing the filars to be bundled in an "untwisted" fashion.

According to another aspect, a wire containing one or more filars may be employed to electrically couple two elements of an implantable medical apparatus such as a lead, lead extension, and catheter for delivering therapy to a patient. For instance, such a wire may be employed to electrically couple a connector electrode and a conducting (stimulation) electrode of an implantable medical electrical lead or lead extension. Such wires may also be used to electrically couple a connector electrode and a sensor carried by a lead, lead extension, or a catheter. Any two elements adapted to perform at least one of receiving and transmitting an electrical signal may be electrically coupled by the various wire configurations described herein.

According to one aspect of the disclosure, an implantable medical apparatus carrying a conducting electrode and a connector electrode is described. The medical apparatus includes a lead body and a wire carried by the lead body. The wire electrically couples the conducting electrode and the connector electrode. This wire comprises a silver core and an MP35N coil positioned around the silver core.

Another aspect of the disclosure relates to an implantable medical lead carrying two elements, each of the elements being capable of at least one of transmitting and receiving an electrical signal. The lead comprises a silver core extending between, and electrically coupling, the two elements. An MP35N coil is wound around, and is electrically coupled to, the silver core. The elements may be a connector electrode and conducting electrode, for instance. In the alternative, the elements may be any other entities capable of receiving, transmitting or conducting an electrical signal.

An implantable medical apparatus is disclosed in another embodiment. The apparatus includes an MP35N coil and a silver core positioned within the coil. According to another aspect, an implantable medical lead is provided that has a core having a resistivity of less than 20 micro-ohms per centimeter and a coil surrounding the core formed of a biocompatible alloy having an ultimate tensile strength of between 150 kilo pounds per square inch (ksi) and 280 ksi at room temperature.

According to yet another embodiment, a method of manufacturing a medical apparatus is described. This apparatus may be, for instance, a lead, a lead extension or a catheter. The apparatus could further be any other type of device that could usefully benefit from a wire that has superior kink resistance of the type described herein. The method includes providing a silver core, winding an MP35N filament around the silver core to form a filar, and including one or more such filars in a wire positioned within a body of the medical apparatus. This method includes annealing MP35N at a temperature above the melting point of the silver core and drawing the MP35N to a diameter of between 0.03 millimeters and 0.10 millimeters to form the filament to wrap around the silver core.

Other aspects of the invention will become apparent to those skilled in the art from the following description and the accompanying drawings.

BRIEF DESCRIPTION OF THE DRAWINGS

FIG. 5A is a side view of one embodiment of a filar according to the current disclosure.

FIG. 5B is a side view of another embodiment of a filar according to the current disclosure.

FIG. 5C is a side view of an embodiment of a filar according to the current disclosure that includes an insulating sheath.

The drawings are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar.

DETAILED DESCRIPTION OF THE INVENTION

Figure 1:
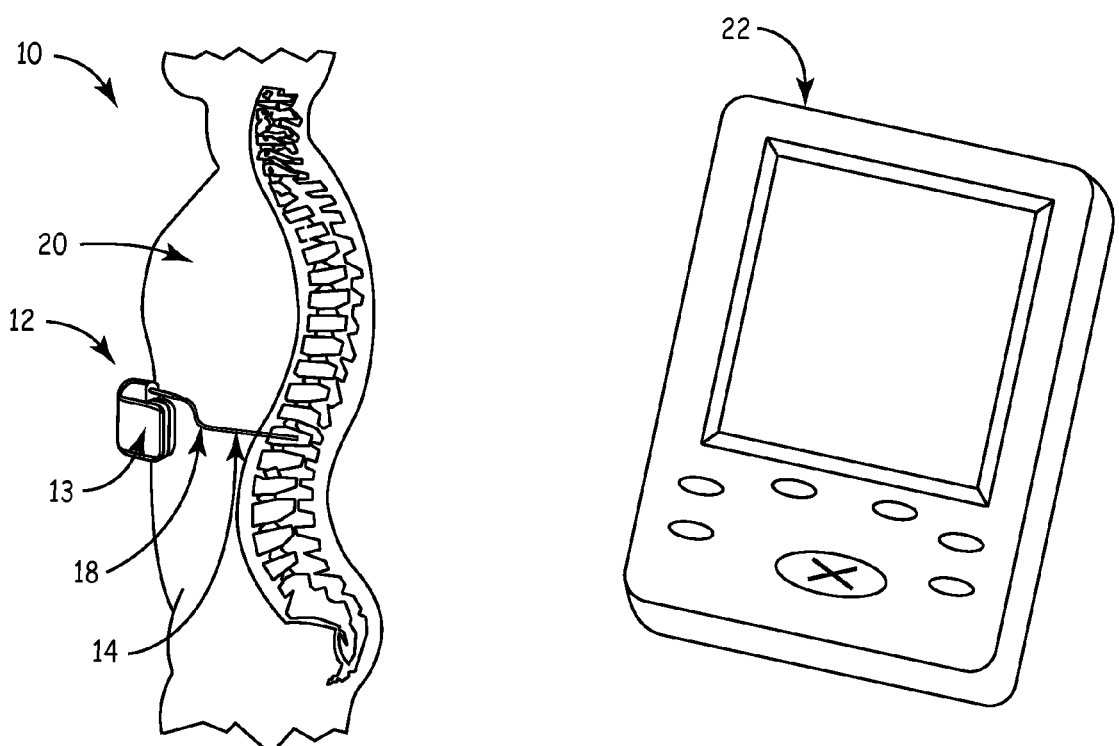
FIG. 1 shows a general environmental view for a neurostimulation system embodiment.

FIG. 1 shows one exemplary environmental view 10 of a neurostimulation system 12 that may usefully employ the techniques and mechanisms of the current disclosure. While this example displays an implantable neurostimulation system embodiment, other medical systems such as cardiac systems, and other systems used to delivery therapy to a living body may employ the concepts disclosed herein.

A neurostimulation system 12 of the type shown in view 10 may be used to treat conditions such as pain, movement disorders, pelvic floor disorders, gastroparesis, incontinence, sexual disfunction, and a wide variety of other medical conditions. This system includes a neurostimulator 13 coupled to a stimulation lead 14. In the current embodiment, coupling is accomplished using a lead extension 18. The neurostimulator 13 is typically implanted subcutaneously in the patient's body 20 at a location selected by the clinician. The stimulation lead 14 is typically fixed in place near the location selected by the clinician using a device such as the adjustable anchor. A programmer 22, which may be a clinician or patient programmer, may be used to program neurostimulation system 12 to deliver electrical stimulation via one or more conducting electrodes located along lead 14.

Figure 2:
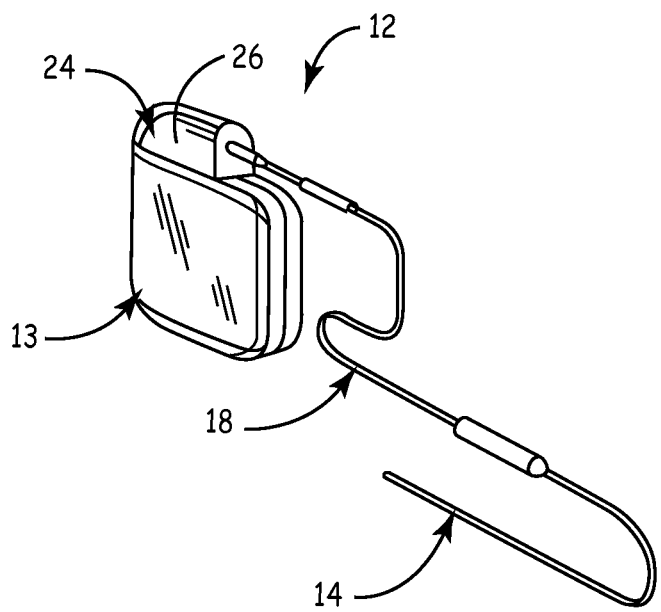
FIG. 2 shows a neurostimulation system embodiment.

FIG. 2 shows an implantable neurostimulation system 12 comprising an implantable neurostimulator 13, a stimulation lead 14, and a lead extension 18. The implantable neurostimulator 13 has a housing 24, a power supply carried in the housing 24, and stimulation electronics which may be provided by the battery and coupled to a connector block 26, which is also known as a terminal block.

Figure 3:
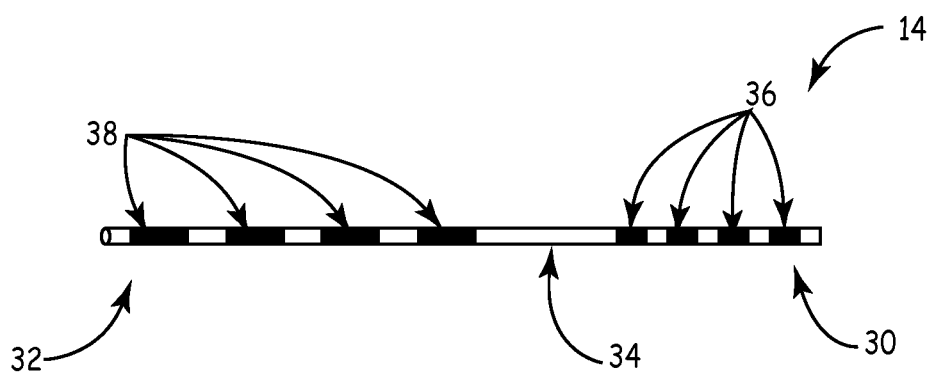
FIG. 3 is a side view of one embodiment of a stimulation lead.

FIG. 3 is a side view of one embodiment of stimulation lead 14. The stimulation lead 14 has a lead proximal end 30, a lead distal end 32 and a lead body 34. The lead distal end 32 has at least one conducting electrode 38 to deliver electrical stimulation to a living body, or to receive an electrical signal from the body. The lead proximal end 30 includes at least one connector electrode 36 (also known as electrical terminals) to electrically couple the conducting electrode 38 to stimulation electronics inside neurostimulator 13, optionally through lead extension 18. There is at least one wire (not shown) contained within lead body 34 that is electrically connecting the at least one connector electrode 36 to the at least one conducting electrode 38.

It is desirable to utilize a material possessing a low resistivity to form the wire. This will result in a minimum voltage drop between the conducting electrode 38 and the connector electrode 36 to which it is coupled. For example silver may be used for this purpose.

Limitations exist with selecting a low-resistivity core alone to serve as the wire. Materials such as silver do not generally exhibit superior toughness or tensile strength characteristics. Therefore, bending and twisting a wire made solely of silver may, over time, result in wire breakage.

One way to address the foregoing limitations is to surround a low-resistivity core (e.g., a silver core) with another material that can provide additional strength.

Figure 4A:
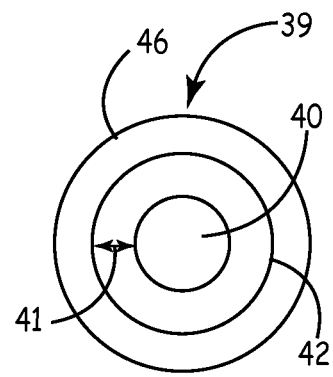
FIG. 4A is a cross-sectional view of one embodiment of a configuration that may be used to electrically couple one or more conducting electrodes to one or more connector electrodes.

FIG. 4A is a cross-sectional view of one embodiment of a wire 39 that may be used to electrically couple one or more conducting electrodes 38 to one or more connector electrodes 36. The wire 39 includes a low-resistivity core 40 that is capable of providing a low-resistant path between a conducting electrode and a connector electrode. The core 40 is threaded into a tube 42 formed of a biocompatible, corrosion-resistant material having a tensile strength that is higher than the core.

Wire 39 may be electrically insulated by a polymer 46. The polymer could be, but is not limited to, ethylene tetrafluoroethylene (ETFE), polytetrafluoroethylene (PTFE), silicone rubber or polyurethane. Other materials that act as electrical insulators may be used in the alternative.

While use of a wire 39 of the type shown in FIG. 4A provides advantages, it is difficult to manufacture. During the manufacturing process, tube 42 is formed that has a diameter of about 0.25 mm-1.02 mm. The low-resistivity core 40 is threaded into this tube. Tube 42 is then heated until is becomes flexible enough to be drawn. The tube 42 and the inner core 40 are drawn to obtain a wire having a smaller diameter. Generally, the steps of heating the tube 42 and the core 40 are repeated multiple times until the tube is of a desired diameter.

As discussed above, to draw the tube 42 to form a wire having the desired diameter, the tube is heated to a desired temperature at which the material becomes flexible. However, materials of the type suitable for use as tube 42 must generally be heated to a relatively high temperature before they can optimally be drawn. For instance, a material such as MP35N may typically be heated to between 1,037° C. and 1,093° C. (or about 1,900° F.-2,000° F.) before being drawn. However, the melting point of low-resistivity materials of the type used to form core 40 is generally below such high temperatures. For instance, the melting point of silver is around 960° C.

As may be appreciated by the foregoing, at the optimal temperature for heating and drawing tube 42, the core material will be liquefied. As a result, some of the liquefied core material may exit (i.e., "run out of") the ends of the tube 42. Moreover, the liquefied core material that is located within the center away from the ends of the tube 42 will expand and exert pressure on the inside of the tube. This creates bulges in the tube 42 before and during the drawing process. The portions of the wire 39 having such imperfections will be discarded after the drawing process is completed, resulting in manufacturing waste and lower yields.

To prevent the foregoing from occurring, heating may be limited to something much less than what is optimal for the material of the tube 42. For instance, heating of a tube 42 formed of MP35N may be limited to prevent melting a silver core. However, at this temperature, the MP35N is relatively brittle, making the material difficult to work, and further complicating the manufacturing process.

Another option for addressing the foregoing challenges may involve threading core 40 into tube 42 after the tube has been drawn to the desired length and diameter. However, after the tube has been drawn, the tube will have a very small diameter and a very long length. This makes the threading process difficult, if not impossible in some cases.

Yet another complication associated with the configuration of FIG. 4A involves impurities such as small dust particles that may be trapped within the center of tube 42 when the tube is formed and before core 40 is inserted. As the core 40 is threaded into tube 42, such impurities become trapped between the core 40 and tube 42. As the tube 42 is heated and then drawn, the particles are drawn along an elongated area of the wire 39. This may result in an area of core 40 exhibiting a higher resistivity than is desired. Further, this may result in an elongated area of tube 42 that has somewhat diminished tensile strength properties One way to prevent such occurrences is to utilize expensive "clean room" processing to minimize particle contamination of tube 42. Additionally, during subsequent testing of the wire 39, any contaminated areas are discarded, leading to material waste and lower yields.

The configuration of FIG. 4A further raises manufacturing issues involving the coupling of wire 39 to electrodes and connectors such as those on lead 14. This may be appreciated by considering FIG. 4B.

Figure 4B:
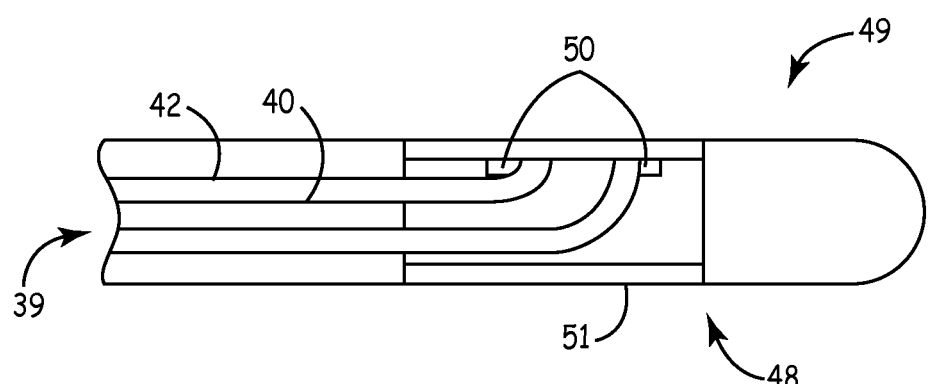
FIG. 4B is a side cutaway view of a distal end of a stimulation lead.

FIG. 4B is a side cutaway view of distal end 48 of lead 49. Lead 49 is shown to carry wire 39 having a low-resistivity core 40 surrounded by tube 42. To affix an end of wire 39 to an inner surface of electrode 51 (also shown cut-away), the end is abutted to the inner surface of the electrode and the tube 42 is heated to create an electrical bond with the inner electrode surface. In one embodiment, conductive joints 50 may be formed around the outside of tube 42 to facilitate this bonding, as by melting one or more beads of material having a high conductivity.

While the configuration shown in FIGS. 4A and 4B provide some desirable properties, this configuration also poses some manufacturing challenges that may require use of expensive processing techniques and/or result in manufacturing waste. The current disclosure provides techniques to address these challenges.

FIG. 5A is a side view of one embodiment of a filar 69 in accordance with the current disclosure. An inner conductive core 62 is provided of a low-resistivity material. In one embodiment, this material possesses a resistivity of less than 20 $\mu\Omega$ per centimeter. For instance, core 62 may be formed of silver. As other examples, the core may be formed of tantalum, tantalum alloys, niobium, niobium alloys, platinum and platinum alloys, and palladium and palladium alloys. Other materials possessing a resistivity of less than 20 $\mu\Omega$ per centimeter may be used instead.

A conductive coil 60 is wound around core 62. For purposes used herein, the term "coil" is used to refer to a series of multiple connected turns formed by gathering or winding. This coil is in contrast to the tube described in reference to FIGS. 4A and 4B which consists of a single elongated cylindrical structure without multiple windings.

In one embodiment, coil 60 is formed of a biocompatible alloy, which may be a super alloy, having an ultimate tensile strength (UTS) of between 150 kilo pounds per square inch (ksi) and 280 ksi at room temperature. Examples of such alloys include CoCrMo, CoFeCrMo, and CoFeNiCrMo. In one specific embodiment, the alloy is MP35N (CoNiCrMo) or a low-titanium ("low-ti") MP35N. Other biocompatible cobalt-based, nickel-based or titanium-based alloys and super alloys may be used in the alternative. For instance, Ti-15Mo is one example of a titanium-based alloy suitable for this purpose.

Coil 60 may be formed of one or more conductive filaments. For purposes of the discussion of FIG. 5A, it will be assumed that coil 60 is formed of a single filament. A multi-filament embodiment is described in reference to FIG. 5B.

According to the disclosure, in preparation to form coil 60, a conductive strand having a starting diameter which may, in one embodiment, range from 0.254 mm to 1.02 mm (about 0.01-0.04 inches), is annealed at a temperature selected based on the material that is being used. For instance, if the selected material is MP35N, the conductive strand will be annealed to between 1,037° C. to 1,093° C. (about 1900° F.-2,000° C.). This temperature will generally be above the melting point of the material used to form core 62. The core material is then drawn to obtain a filament having some desired diameter.

The drawing process is generally iterative such that the conductive alloy will be heated and drawn several times until a filament of the desired diameter is obtained. In general, it is desirable to obtain a filament having a diameter as small as possible, since a coil formed of a small diameter filament will withstand more bend stress than one formed of the same material but which has a larger diameter. There are limits, however, on the diameter that may be reasonably achieved, since beyond some lower limit, the filament will be so thin that it will be vaporized when subjected to high temperatures. In view of these competing considerations, in one embodiment, the diameter of the filament following the annealing process will be between 0.025 millimeters and 0.102 millimeters (about 0.001 inches-0.004 inches). Preferably the diameter will be between 0.025 mm and 0.051 mm (about 0.001 inches-0.002 inches). In one specific embodiment, this diameter is 0.033 mm (about 0.0013 inches).

After the conductive material that will be used to form the coil is drawn to obtain the filament of a desired diameter, this filament is wound around core 62. This is accomplished by exerting enough force on either end of core 62 to remove slack. While this force is maintained on core 62, the filament is wound around core 62 at a desired angle θ 63. This angle 63 may be measured with respect to a cross-sectional axis 65 that is perpendicular to the longitudinal axis 67 of core 62. In one embodiment, this angle is selected to be between 0 and 45°.

Selection of angle θ 63 may take into account several considerations. When the angle θ 63 is selected to be zero such that the coil windings are substantially parallel to cross-sectional axis 65, conductor coil 60 is able to withstand a high level of stress. In this case, when force is exerted on filar 69, conductor coil 60 is readily able to expand a maximum amount without breaking or becoming permanently deformed. A disadvantage to this configuration, however, relates to the amount of material required to form coil 60. The amount of material needed for this purpose increases as angle θ 63 decreases. Thus, material costs are reduced when angle θ 63 is chosen to be somewhat greater than zero.

While selecting an angle θ 63 that is somewhat above zero will decrease material costs, selecting an angle that is too large will increase manufacturing complexity. This is particularly true when coil 60 is formed of a single filament (rather than of multiple filaments as will be described in reference to FIG. 5B). When coil 60 is formed of a single filament, it is difficult to maintain the single filament at an angle that is above about 30° during the winding process. To achieve a greater angle in a single-filament embodiment, a special winding mechanism must be used that increases production costs. Therefore, attempting to increase the angle too much to save material costs will have the adverse effect of increasing manufacturing complexity. For this reason, when coil 60 is formed of a single filament, it is desired to select angle θ 63 to be between zero and 30 degrees.

As mentioned above, in some embodiments, more than one conductor filament is used to form coil 60. This is described in reference to FIG. 5B.

FIG. 5B is a side view of a filar 71 according to another embodiment of the current disclosure. A core 62 is formed of a low-resistivity material in the manner described above. This core 62 is surrounded by a coil 66 formed of N filaments wherein N is "four" in the current example, as shown by the four filaments 66a-66d that are being used to create the windings.

For a given coil, each of the N filaments is formed by heating and drawing a conductive strand in a manner similar to that described above. The conductive strand is made of a biocompatible alloy having a UTS between 150 ksi and 280 ksi as previously discussed.

In one embodiment, N filaments that have substantially the same diameter and that are formed of the same material are positioned side-by-side and coiled around core 62 at a same time, as shown in FIG. 5B. Winding all filaments at once in this manner is preferable because it saves time and helps maintain alignment. While the filaments could instead be wound one at a time, the winding process would take longer to complete, and the spacing of the filaments would be more difficult to control, adding complexity to the process.

As was the case with the embodiment of FIG. 5A, filaments 66a-66d may be wound at an angle θ 63 measured from cross-sectional axis 65. In general, when N is selected to be something greater than one, angle θ 63 must be greater than zero. Moreover, as N increases, angle θ must also increase.

When conductors 66a-66d are wound around core 62 to create coil 66, gaps may be created between each set of windings. This is as represented by arrows 64. The likelihood that such gaps will exist typically increases as N increases and as angle θ 63 increases.

When multiple filaments are used to form coil 66 as shown in FIG. 5B, the coil is easier to wind and the winding can be completed faster. Moreover, less material is typically required to form coil 66 because of the increasing angle θ 63 that is associated with use of multiple filaments. However, this type of a multi-conductor coil 66 will generally not be able to tolerate as much stress as a coil formed of a single conductor with angle θ 63 being at, or close to, zero.

As may be appreciated, competing considerations are involved in choosing a configuration for coil 66 that results in a high-stress kink-resistant filar that is easy to manufacture and is also cost effective. In one particular embodiment, coil 66 is formed of between 2 and 4 filaments and has an angle θ 63 between 5° and 45°.

FIG. 5C is a side view of a filar 72 according to another embodiment of the disclosure. The filar includes a core 62. A coil 74 may be wound around core 62 using any of the approaches discussed above with respect to FIGS. 5A and 5B.

Filar 72 is surrounded by a polymer layer 76 (shown cutaway). The polymer may be, but is not limited to, ethylene tetrafluoroethylene (ETFE), polytetrafluoroethylene (PTFE), silicone rubber or polyurethane. Any other material that acts as an electrical insulator and that is suitable for medical applications may be used for this purpose.

The embodiments shown in FIGS. 5A-5C provide various performance and manufacturing advantages over the designs shown in FIGS. 4A and 4B. Most notably, the one or more filaments used to form the coil may be annealed and drawn at any temperature that is optimal for the material being used to form the coil. Melting of the core will not occur during drawing of the filaments since the filaments are not in contact with the core at the time of annealing. This is highly advantageous since alloys of the type described herein to form the coil are optimally drawn at temperatures well above the melting point of low-resistivity materials of the type used to form the cores.

In addition to the foregoing, a coil configuration of the type shown in FIGS. 5A-5C will exhibit far greater elasticity than a tubular configuration of the same material. For instance, a tube 42 of MP35N having a configuration similar to that shown in FIGS. 4A and 4B will have an elasticity of approximately 0.1%. This means that when force is exerted on the conductor, the conductor will only stretch about 0.1% of its total length before breaking. In contrast, a coil that is formed of an MP35N conductor having a diameter approximately the same as the tube of the foregoing example has an elasticity of about 8%. Thus, the coil will stretch about 8% of its total length before breaking when the coil undergoes stress. Thus, the coil configuration shown in FIGS. 5A-5C is able to withstand much more force, both in the longitudinal as well as in the lateral directions, than the configuration of FIGS. 4A-4B.

Other advantages relate to particle contaminants. As discussed above, particles that become trapped within tube 42 (FIGS. 4A and 4B) become embedded in an elongated portion of the tube during the heating and drawing process. This may result in a portion of core 40 that has a higher-than-expected resistivity, and may further result in a portion of tube 42 that has a lower-than-expected UTS. To prevent such occurrences, more expensive "clean-room" techniques may be implemented, which is not desirable.

Embodiments of the current disclosure largely eliminate issues associated with particle contamination. During the drawing process used to create the one or more filaments that are incorporated into a coil, particles that are located on an exterior surface of the alloy are burned off as the filaments are drawn. These particles are not incorporated into, and do not substantially affect, the UTS or other properties of the drawn filaments. Moreover, particles located on the surface of core 62 that are trapped between the core 62 and a coil (e.g., coil 60, 66, or 74) during the winding process will not substantially affect performance of the filar. Specifically, the particles do not affect the composition of the coil material to decrease elasticity or tensile strength of the coil. Likewise, these particles do not affect the composition of core 62 and thus will not increase resistivity of the core.

Figure 5D:
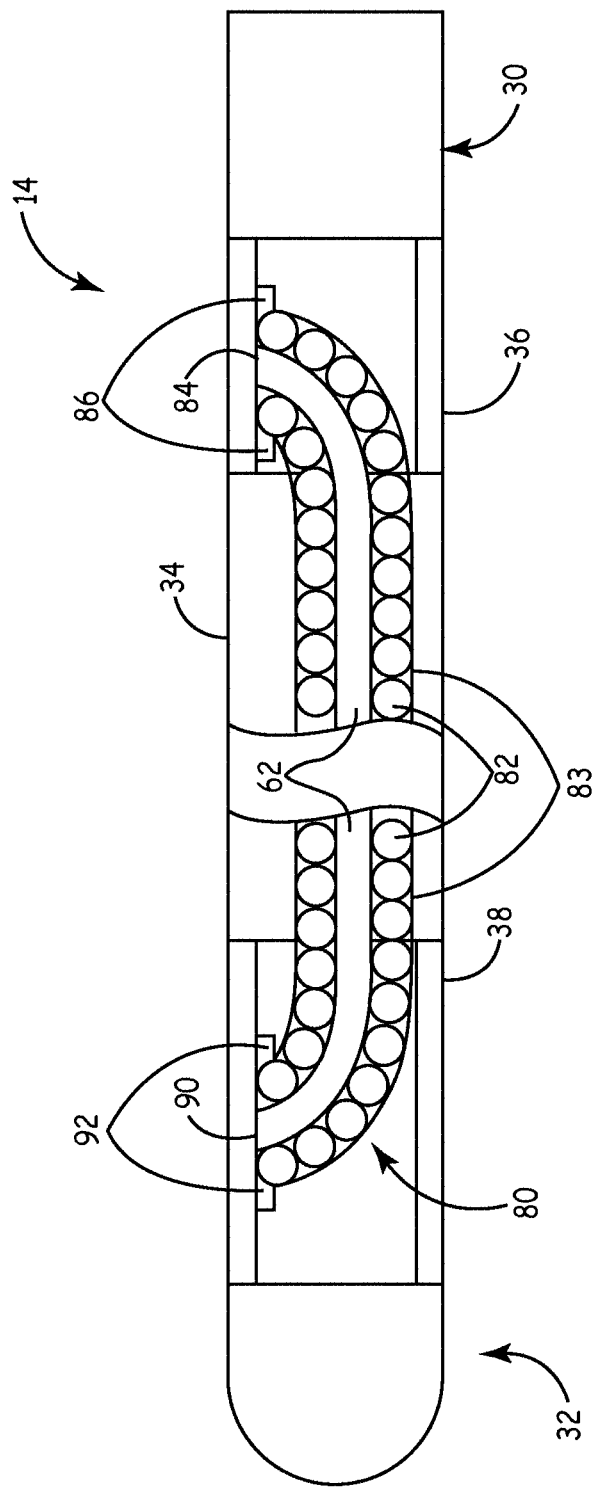
FIG. 5D is a side cutaway view of a medical electrical lead that includes a wire according to one embodiment of the current disclosure.

Yet another advantage of the process of the current disclosure may be appreciated by considering FIG. 5D.

FIG. 5D is a side cross-sectional view of lead 14 similar to that shown in FIG. 3 that includes a wire 80 having a single filar. This filar includes a core 62 around which a coil 82 is wound according to any of the embodiments shown in FIGS. 5A-5C. The core 62 and coil 82 are surrounded by a polymer layer 83, which may be polyurethane, silicone, or another type of polymer suitable for implantable medical apparatus.

A proximal end 30 of lead includes a connector electrode 36, which may be a ring connector (shown in cross-section) or any other type of connector electrode suitable for a medical electrical lead. Such a connector electrode may be used to mate with a corresponding connector of a pulse generator or lead extension, for instance. In this manner, the connector electrode 36 may be coupled to receive a signal from, or provide a signal to, the pulse generator. The pulse generator may be any type of pulse generator for providing therapy to a patient, including, but not limited to, those described herein.

An end 84 of wire 80 is abutted next to an inner surface of connector electrode 36. This end may be heated by a resistive or a laser welding process. This will bond end 84 to this surface, forming an electrical and mechanical connection. This bonding may be further strengthened by melting beads of a fusible metal alloy to form electrically conductive joints 86. For instance, beads of a high-conductivity material may be melted to form these conductive joints.

Also shown in FIG. 5D is a distal end 32 of lead 14 that includes a conducting electrode 38 to deliver therapy to a body or receive a signal from a body. Such an electrode may be a ring electrode (shown in cross-section) or any other type of electrode suited for a medical electrical lead. An end 90 of wire 80 is abutted next to an inner surface of electrode 38. This end may be heated by a resistive or a laser welding process. This will bond end 90 to this surface of the conducting electrode, forming an electrical and mechanical connection. This bonding may be further strengthened by melting beads of a fusible metal alloy to form electrically conductive joints 92.

The bond to electrode 38 may be formed more readily with the configuration of FIGS. 5A-5C as compared to that of FIGS. 4A and 4B. This is because the windings around core 62 provide more material with which to work during the laser welding process. In particular, because of the coil configuration, a full diameter of the conductive filament used to form coil 60 surrounds all sides of core 62, providing more material for creating the bond to electrode 38. This is in contrast to the configuration of FIGS. 4A and 4B, wherein the material to form the weld is limited to the diameter of core 40 and the width 41 (FIG. 4A) of the surrounding tube 42.

The lead of FIG. 5D further includes an insulating lead body 34. This may be formed of any of the biocompatible polymer materials suitable for medical electrical leads, as described herein.

While the lead embodiment of FIG. 5D is intended to provide one example of techniques discussed herein, it will be appreciated that such mechanisms may be applied to many other embodiments. For instance, while the embodiment of FIG. 5D is a simple example showing a wire having a single filar, wires having more than one filar of the type discussed above may be used to electrically couple any two or more elements. Any elements that are each capable of receiving and/or transmitting an electrical signal, including connector electrodes, conducting electrodes, sensors, and the like may be coupled in this manner. Such elements may be carried by medical apparatus such as implantable leads, lead extensions, catheters, and the like. Moreover, a medical apparatus may carry multiple wires. For instance, for a lead having multiple pairs of conducting and connector electrodes, a respective single- or multi-filar wire may be provided for each such electrode pair.

From the foregoing it will be apparent that the wire described herein provides superior performance while resulting in a stream-lined manufacturing process. In particular, a core 62, which may be formed of silver or some other conductor, provides a very low resistance path between a connector electrode 36 of lead 14 and a corresponding conducting electrode 38. A coil (e.g., 60, 66, 74) formed of a biocompatible alloy such as MP35N that is wound around the core 62 adds significant strength, elasticity, kink and strain resistance to the core 62. These benefits are achieved using manufacturing techniques that allow the conductor used to form the coil to be heated independently of core 62, thereby resulting in a manufacturing process that is much easier to control and may be completed more efficiently. Use of the coil further addresses issues associated with particle contamination. This further helps to streamline the manufacturing process.

Multiple filars of the type described in reference to FIGS. 5A-5C may be incorporated into a single wire. This is discussed in reference to FIGS. 6A and 6B.

Figure 6A:
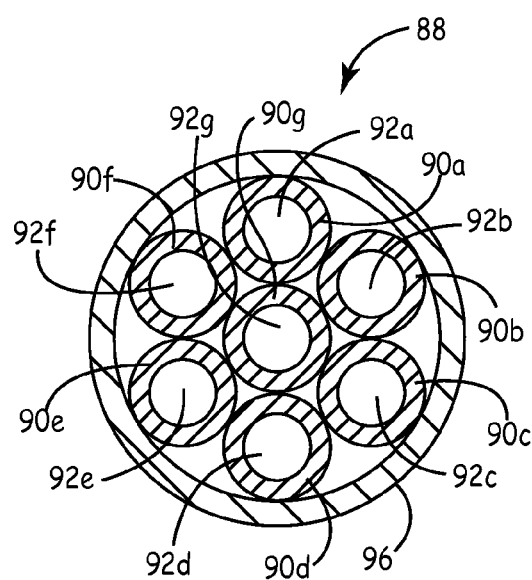
FIG. 6A is a cross-sectional view of one embodiment of a wire according to the current disclosure.

FIG. 6A is a cross-sectional view of one embodiment of a wire according to the current disclosure. The wire 88 includes multiple filars that may be of any of the types described in reference to FIGS. 5A-5D. In this embodiment, seven filars are shown, each having a respective one of cores 92a-92g, and each further having a respective one of coils 90a-90g wound around the corresponding core. The seven filars are surrounded by a single polymer sheath 96, which may be, but is not limited to, ethylene tetrafluoroethylene (ETFE), polytetrafluoroethylene (PTFE), silicone rubber or polyurethane. Other materials that act as electrical insulators may be used in the alternative.

All of the seven filars within wire 88 may be electrically coupled to one another. Each of these filars may then be electrically coupled to the same set of elements to provide redundancy. For instance, each of the filars may be electrically coupled to a same one of connectors 36 and a same one of electrodes 38. In this manner, wire 88 provides a high degree of reliability. In particular, failures may occur in up to six of the filars of wire 88 without experiencing an open circuit, so long at one of the filars is still electrically coupling the connector 36 and the corresponding electrode 38.

In another embodiment, at least one of the filars that are bundled together in the manner shown in FIG. 6A may be provided with a respective insulating sheath so that this filar is not electrically coupled to at least some of the other filars included in the same bundle. This may allow the insulated filar to be used to electrically couple one set of elements while other ones of the filars within the same bundle are used to electrically couple a different set of elements.

Any desired degree of redundancy may be provided by a wire of the type shown in FIG. 6A that includes N filars, wherein N is more than one. If no redundancy is required, the wire may include only a single filar such that N is "one".

Figure 6B:
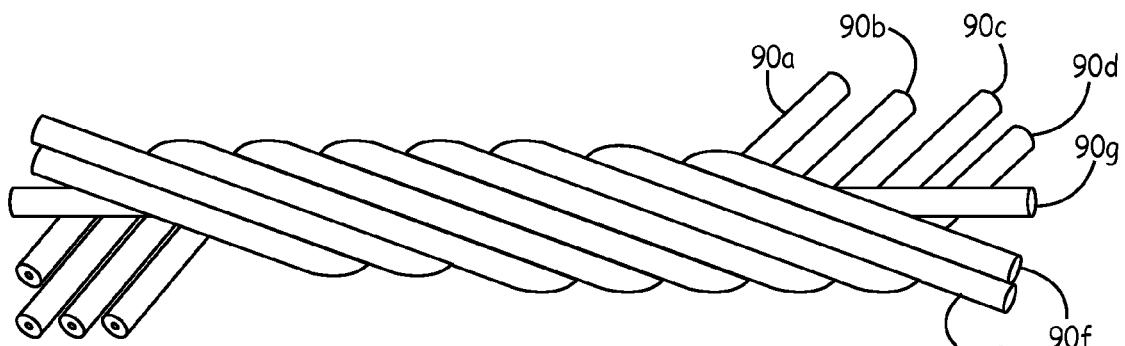
FIG. 6B is a side view of one embodiment of a wire in a twisted cable configuration according to the current disclosure.

FIG. 6B is a side view of a wire according to one embodiment of the disclosure. This wire includes the multiple filars shown in FIG. 6A being configured in a twisted cable arrangement. In particular, the filar formed of coil 90*g* and corresponding core 92*g* (not shown in this view) is located substantially in the center of the wire. The remaining coils 90*a*-90*f* and respective cores 92*a*-92*f* are twisted around this center filar. As described in reference to FIG. 6A, the resulting wire may be surrounded by an insulating sheath 96. In one embodiment wherein such a wire is located within a medical device, the body of the medical device may optionally serve as the insulating sheath.

Figure 7:
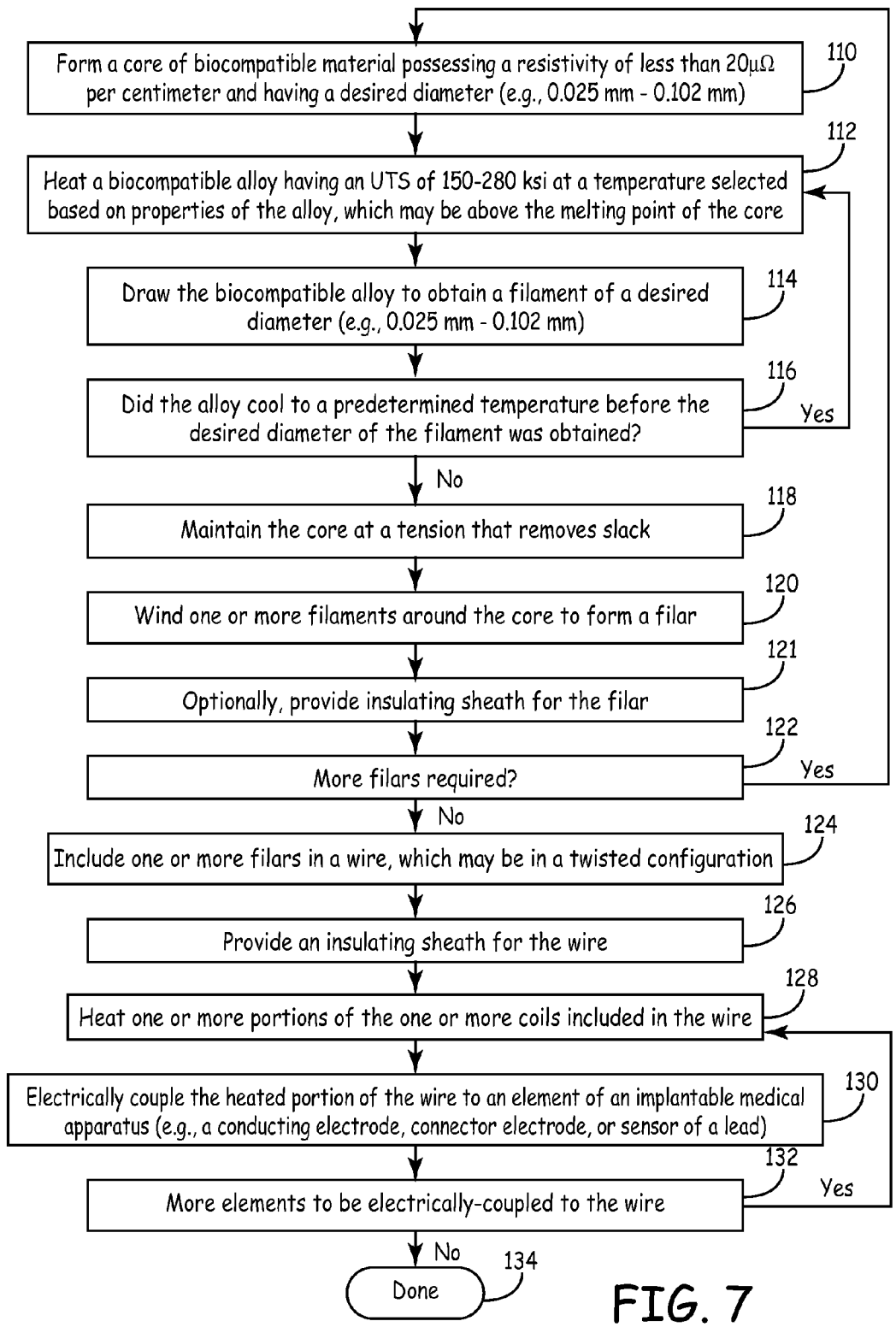
FIG. 7 is a flow diagram of a manufacturing process according to one embodiment of the current disclosure.

FIG. 7 is a flow diagram of one method of manufacturing a filar and a wire according to one embodiment of the disclosure. A core of biocompatible material possessing a resistivity of less than 20 μΩ per centimeter is formed (110). Silver may be used for this purpose, although any material possessing this low resistivity may be used in the alternatively. For instance, any of tantalum, tantalum alloys, niobium, niobium alloys, palladium and palladium alloys may be used instead of silver to form the core.

This core may be formed by cold-working the material, or by heating and drawing it. The diameter of the final core is use-dependent and may range in one embodiment from 0.025 millimeters to 0.102 millimeters (about 0.001 inches-0.004 inches). In one particular embodiment, the core has a diameter of 0.033 millimeters (about 0.0013 inches).

A biocompatible alloy having a UTS of between 150 and 280 ksi may be annealed at a temperature that is selected based on properties of the selected alloy (112). Generally, this temperature will be above the melting point of the core material used to form the core in step 110. The biocompatible alloy selected for this purpose may be a cobalt-based alloy or super alloy such as MP35N or a low-ti MP35N. In one alternative embodiment, the alloy or super alloy may be a cobalt-based alloy that substitutes iron for nickel. Any biocompatible cobalt-based, nickel-based or titanium-based alloys and super alloys may be used, such as Ti-15Mo.

Once the selected alloy is annealed, it may be drawn to obtain a filament of a desired diameter (114). For instance, the filament may be drawn to obtain a diameter of between 0.025 millimeters and 0.102 millimeters (about 0.001 inches-0.004 inches). It is generally desirable to obtain a filament having as small a diameter as possible so that the resulting coil exhibits maximum elasticity. In a more specific embodiment, the diameter will be between 0.025 millimeters and 0.051 mm (about 0.001 inches-0.002 inches). In a particular embodiment, the diameter is 0.033 mm (about 0.0013 inches).

If the alloy cools to a predetermined temperature before the desired diameter of the filament is obtained (116), steps 112 and 114 may be repeated multiple times to obtain the target diameter. Drawing must cease when the filament is drawn to a diameter that is too thin to allow the filament to be re-heated without vaporizing.

The core is maintained at a tension that removes slack (118). While the core is maintained at this tension, one or more filaments formed according to steps 112 and 114 are wound around the core to form a filar (120). These filaments are preferably both electrically and mechanically coupled to the core. This winding will occur at a selected angle θ that may be measured from a cross-sectional axis that is substantially perpendicular to the longitudinal axis of the core. This angle will, in part, be determined by the number of filaments that are wound around the core, with the angle increasing as the number of filaments increases. If desired, an insulating sheath may be provided for the filar (121).

If multiple filars are to be formed according to the foregoing steps (122), processing returns to step 110. After all filars are available, one or more of the filars may be included in a wire (124). For instance, multiple filars may be twisted together into a wire that has a cable arrangement. Alternatively, the filars may be bundled in a configuration that is not twisted. If desired, a first subset of the filars in a wire may be electrically insulated from a second subset, as by providing one or more insulating sheaths surrounding respective subsets of the filars. Any number of such electrically-insolated subsets of filars may be included in a single wire.

An electrically insulating sheath may be provided around all of the one or more filars that form the wire (126). This insulating sheath may be formed of a biocompatible material such as PTFE, ETFE, silicone, and so on. This sheath may serve as the lead body when the wire is being used within a medical electrical lead.

This wire may be utilized to electrically couple multiple elements of a medical apparatus to one another. This is accomplished by heating one or more portions of the coils of the wire, preferably without melting the cores (128). The heated portion of the wire may be electrically coupled to an element of a medical apparatus, which may be a lead, lead extension, catheter, and the like (130). Steps 128 and 130 may be repeated as needed to electrically couple multiple elements of the medical apparatus to one another (132). When all required elements have been electrically coupled, the process is complete (134).

According to steps 128-132, the wire may be employed to electrically couple a connector electrode of a medical electrical lead to one or more corresponding conducting electrodes. The conducting electrodes may be sensing and/or therapy delivery electrodes. In another embodiment, the wire may be used to electrically couple other types of elements in other types of medical devices. For instance, this wire may be used to electrically couple a connector electrode of a catheter to a sensor carried by the catheter. This sensor may be any type of sensor that needs to exchange one or more electrical signals with the connector electrode. In general, an element that is coupled by wire may be any element capable of receiving, transmitting, and conducting an electrical signal.

Figure 8:
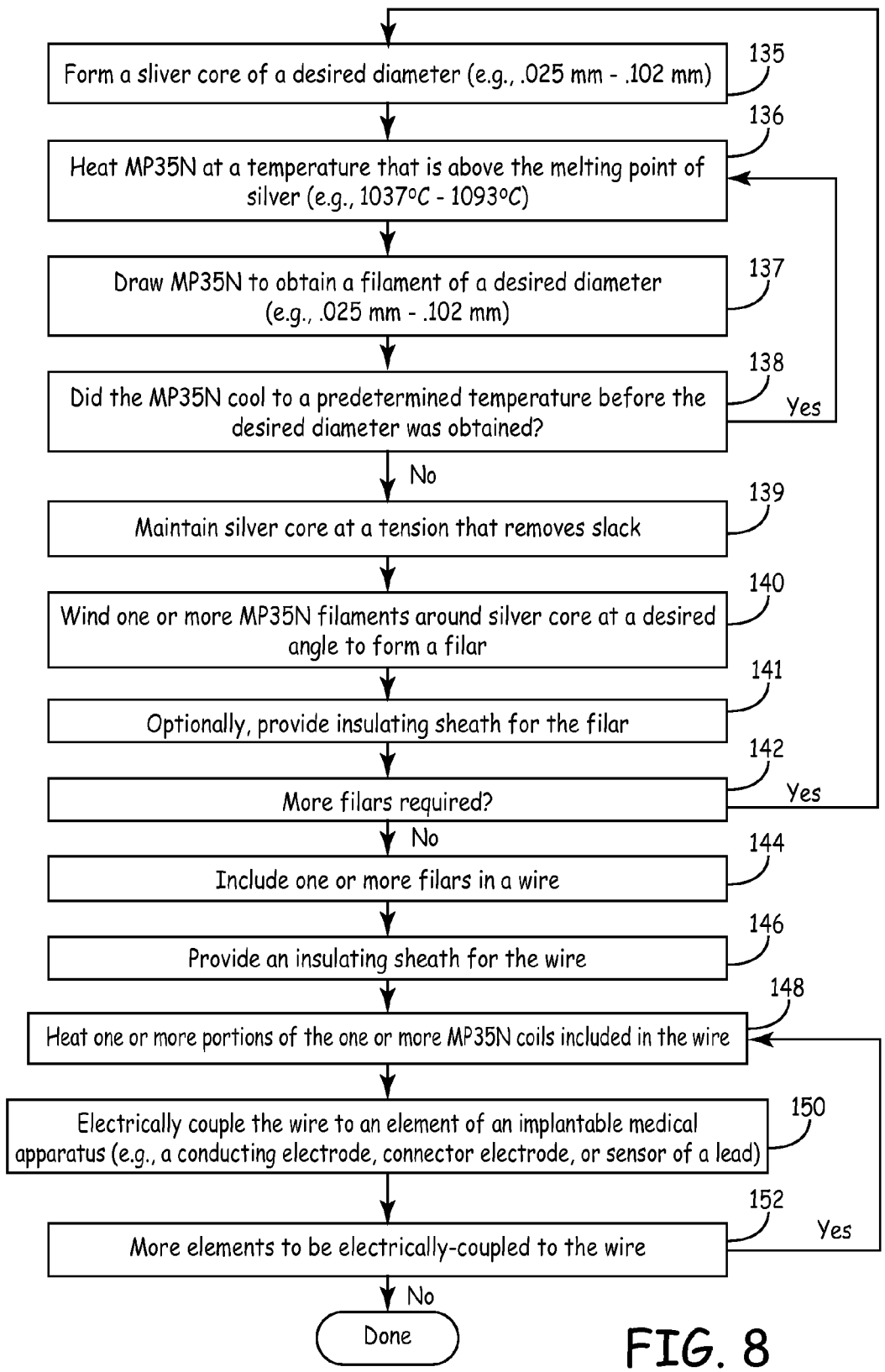
FIG. 8 is a flow diagram of another embodiment of a manufacturing process according to the current disclosure.

FIG. 8 is a flow diagram of a manufacturing process according to one specific embodiment of the current disclosure. According to this embodiment, a core may be formed of silver (135). This core may be formed by cold working the silver, or by some type of heating process. This core may have a diameter ranging from between 0.025 mm to 0.102 mm (or about 0.001 inches-0.004 inches), for instance.

MP35N is annealed at an optimal temperature needed to drawn the MP35N into a filament having a desired diameter (136). In one embodiment, the temperature used for this purpose is above the melting point of the silver. For instance, the MP35N may be annealed at between 1,037° C. and 1,093° C. (or about 1,900° F.-2,000° F.).

After being annealed at the required temperature, the MP35N is drawn to obtain a filament of desired diameter (137). In one embodiment, a diameter of between 0.025 millimeters and 0.102 millimeters (or about 0.001 inches-0.004 inches) is required. According to a more specific embodiment, the diameter of the MP35N filament may be between 0.025 mm and 0.051 mm (about 0.001 inches-0.002 inches). In a more particular embodiment, the diameter may be about 0.033 mm (about 0.0013 inches). Other diameters may be used in the alternative.

If the MP35N cools below some minimum temperature below which the material becomes too brittle to be readily worked and the filament has not yet been drawn to the desired diameter (138), the annealing and drawing steps are repeated. This minimum temperature may be about 1800° F. in one embodiment, although other minimum temperatures may be selected. The reheating and drawing steps will be repeated until a filament of the desired diameter is obtained.

Next, the silver core is held so that tension is exerted along its longitudinal axis to remove slack (139). One or more MP35N filaments that are formed according to the foregoing steps are wound around the silver core at a selected angle to form a filar (140). The silver core and MP35N coil of this filar are electrically and mechanically coupled. The angle used to form the coil will be determined, at least in part, based on the number of filaments that are wound around the core, with the angle generally increasing as more filaments are used for this purpose. If desired, an insulating sheath may be provided for the filar (141).

If more filars are to be formed (142), the processing returns to step 135 and another filar is created according to the foregoing steps. Then one or more filars may be included in a wire (144). For instance, the one or more filars may be twisted together to form the wire. Alternatively, the filars may be bundled in an untwisted configuration. If desired, a first subset of the filars in a wire may be electrically insulated from a second subset, as by providing one or more insulating sheaths surrounding respective subsets of the filars. Any number of such electrically-insolated subsets of filars may be included in a single wire.

The wire may be enclosed within an insulating sheath, if desired (146). Such a sheath may be formed of ETFE, PTFE, silicone, or any of the other insulating materials that are described herein. In one embodiment wherein the wire is being employed in a lead, the insulating sheath is the exterior insulating sheath of the lead.

One or more portions of the coils of the wire may be heated, preferably without melting the cores (148). The heated portion of the wire may be electrically coupled to an element of a medical device (150). Steps 148 and 150 may be repeated as needed to electrically couple multiple elements of the medical device to one another (152).

As was the case described in reference to FIG. 7, the wire constructed according to the method of FIG. 8 may be employed to electrically couple a connector electrode of a medical electrical lead to one or more corresponding conducting electrodes. The conducting electrodes may be sensing and/or therapy delivery electrodes. In another embodiment, the wire may be used to electrically couple other types of elements in other types of medical devices. For instance, this wire may be used to electrically couple a connector electrode of a catheter to a sensor carried by the catheter. This sensor may be any type of sensor that needs to exchange one or more electrical signals with the connector. These signals include, but are not limited to, those used to deliver and/or control therapy, and data signals obtained by a sensor used for diagnosis and monitoring purposes.

It may be appreciated that in the methods described above, some of the steps may be re-ordered within the scope of the invention. Moreover, some steps may be omitted entirely. For instance, in some cases, the insulating sheath need not be provided specifically for the wire, as the body of the medical device (e.g., lead) in which the wire will be used will serve as this purpose. Similarly, those skilled in the art will recognize that the filars and wires described herein may be used to couple other types of elements besides connectors and electrodes, such as sensors, or any other type of component that is intended to transmit, receive, or conduct an electrical signal. Moreover, the disclosed embodiments need not be limited to use in medical electrical leads, but may be used in any other type of medical apparatus carrying such elements, such as catheters. Thus, the embodiments discussed above are merely exemplary, with the scope of the invention to be defined by the Claims that follow.

What is claimed is:

1. An implantable medical apparatus, comprising:
a conductive wire, the conductive wire comprising:
an MP35N (CoNiCrMo) coil; and
a silver core having a length, the silver core positioned within, and electrically coupled to, the coil;
wherein the MP35N coil is directly adjacent to, and extends substantially the length of, the silver core and wherein turns of the MP35N coil are disposed at an angle of between 0 and 45 degrees relative to an axis that is substantially perpendicular to a longitudinal axis of the silver core.

2. The apparatus of claim 1, further comprising:
a connector electrode; and
an element to perform at least one of receiving, transmitting, and conducting an electrical signal; and wherein at least one of the MP35N coil and the silver core electrically couple the connector electrode to the element.

3. The apparatus of claim 2, wherein the element is a conducting electrode or a sensor.

4. The apparatus of claim 1, wherein the MP35N coil and the silver core are electrically and mechanically coupled.

5. The apparatus of claim 1, further comprising:
multiple MP35N coils; and
multiple saver cores, each positioned within a respective one of the multiple MP35N coils.

6. The apparatus of claim 1, wherein the MP35N coil is formed only of one or more MP35N filaments.

7. An implantable medical apparatus carrying two elements, each of the elements being capable of at least one of receiving, transmitting, and conducting an electrical signal, the apparatus comprising:
a conductive wire, the conductive wire comprising:
a silver core having a length, the silver core extending between, and electrically coupling, the two elements; and
an MP35N (CoNiCrMo) coil directly adjacent to, and wound around substantially the length of, and electrically coupled to, the silver core, wherein turns of the MP35N coil are disposed at an angle of between 0 and 45 degrees relative to an axis that is substantially perpendicular to a longitudinal axis of the silver core.

8. The apparatus of claim 7, further comprising:
multiple silver cores extending between, and electrically coupling, the two elements; and
for each of the multiple silver cores, a respective MP35N coil wound around, and electrically coupled to, the respective silver core.

9. The apparatus of claim 8, wherein the MP35N coils and silver cores are twisted together in a wire.

10. The apparatus of claim 7, wherein the MP35N coil is formed of a single filament.

11. The apparatus of claim 7, wherein the MP35N coil is formed of multiple filaments.

12. The apparatus of claim 7, wherein the MP35N coil is formed only of one or more MP35N filaments.

13. The apparatus of claim 7, further including an electrically insulating polymer sheath surrounding the MP35N coil.

14. The apparatus of claim 7, further including at least one electrically-conductive joint formed of a fusible metal alloy bonding the MP35N coil to at least one of the two elements.

15. The apparatus of claim 7, wherein the coil is formed of an MP35N filament drawn to a desired diameter at a temperature that is above the melting point of the silver core.

16. The apparatus of claim 15, wherein the desired diameter is between 0.025 millimeters and 0.102 millimeters.

17. An implantable medical apparatus carrying a conducting electrode and a connector electrode, comprising:
   a body of the apparatus; and
   a conductive wire carried by the body and electrically coupling the conducting electrode and the connector electrode, the conductive wire comprising:
      a silver core having a length; and
      an MP35N (CoNiCrMo) coil positioned directly adjacent to, and around substantially the length of, and electrically coupled to, the silver core, wherein turns of the coil are disposed at an angle of between 0 and 45 degrees relative to an axis that is substantially perpendicular to a longitudinal axis of the silver core.

18. The apparatus of claim 17, wherein the conductive wire comprises multiple filars each comprising a respective silver core and an MP35N coil positioned around the silver core.

19. The apparatus of claim 18, wherein a first subset of the multiple filars is electrically insulated from a second subset of the multiple filars.

20. The apparatus of claim 18, further comprising an insulating sheath to electrically isolate at least one of the multiple filars from another of the multiple filars.

21. The apparatus of claim 17, wherein the MP35N coil is formed of a single filament.

22. The apparatus of claim 17, wherein the MP35N coil is formed of multiple filaments.

23. The apparatus of claim 17, wherein the MP35N coil is formed only of one or more MP35N filaments.

24. The apparatus of claim 17, wherein the MP35N coil is formed of a filament having a diameter of between 0.025 millimeters and 0.102 millimeters.

25. The apparatus of claim 17, wherein turns of the coil are disposed at an angle of between 0 and 45 degrees relative to an axis that is substantially perpendicular to a longitudinal axis of the body.

26. The apparatus of claim 17, wherein the coil is formed of an MP35N filament that is annealed at a temperature exceeding the melting point of the silver core.

27. A method of manufacturing a implantable medical apparatus, comprising:
   obtaining a silver core having a length;
   winding an MP35N (CoNiCrMo) filament directly adjacent to and around substantially the length of the silver core to form a coil that is electrically coupled to the silver core, wherein the coil and the silver core comprise a conductive wire and wherein turns of the coil are disposed at an angle of between 0 and 45 degrees relative to an axis that is substantially perpendicular to a longitudinal axis of the silver core; and
   including the wire within a body of the implantable medical apparatus.

28. The method of claim 27, wherein the medical apparatus has a connector electrode and a conducting electrode, and further comprising electrically coupling the connector electrode and the conducting electrode via the wire.

29. The method of claim 28, further comprising forming an electrically-conductive joint to bond the wire to one of the connector electrode and the conducting electrode.

30. The method of claim 27, further comprising:
   annealing MP35N at a temperature above the melting point of the silver core; and
   drawing the MP35N to a diameter of between 0.025 millimeters and 0.102 millimeters to form the filament.

31. The method of claim 27, further comprising:
   providing multiple silver cores;
   providing multiple MP35N filaments;
   winding each of the multiple MP35N filaments around a respective one of the multiple silver cores to form a respective coil of a respective filar; and
   forming the conductive wire of the multiple filars.

32. The method of claim 27, further including winding multiple MP35N filaments around the silver core to form the coil of the conductive wire.

33. The method of claim 27, further comprising winding only one or more MP35N filaments to form the coil.

* * * * *